United States Patent
Teodorescu

[19]

[11] Patent Number: 5,986,549
[45] Date of Patent: Nov. 16, 1999

[54] POSITION AND MOVEMENT REASONANT SENSOR

[76] Inventor: Horia-Nicolai Teodorescu, 6600 Iasi, Street Balcescu 30, Romania

[21] Appl. No.: 09/004,108

[22] Filed: Jan. 7, 1998

Related U.S. Application Data

[60] Provisional application No. 60/053,543, Jul. 23, 1997.

[51] Int. Cl.⁶ .................................................. G08B 13/26
[52] U.S. Cl. ...................... 340/561; 340/541; 340/680; 340/686.6; 324/207.18; 324/207.16; 324/234; 324/232; 324/236; 324/662; 324/327
[58] Field of Search ..................... 340/561, 541, 340/680, 568, 686.6, 518; 331/65; 307/652, 116; 324/207.18, 207.16, 234, 662, 327, 232, 236; 327/455, 476, 497, 587, 588, 517; 294/907; 361/179; 901/46

[56] References Cited

U.S. PATENT DOCUMENTS

| | | | |
|---|---|---|---|
| 3,371,272 | 2/1968 | Stanton | 324/207.18 |
| 3,745,379 | 7/1973 | Gross | 327/455 |
| 3,852,662 | 12/1974 | Katz | 324/234 |
| 3,986,104 | 10/1976 | Randolph, Jr. | 324/327 |
| 3,997,835 | 12/1976 | Ando et al. | 324/207.26 |
| 4,267,522 | 5/1981 | Periot | 331/65 |
| 4,328,433 | 5/1982 | Nodera et al. | 340/541 |
| 4,474,185 | 10/1984 | Diamond | 600/535 |
| 4,502,042 | 2/1985 | Wührl et al. | 340/561 |
| 4,895,160 | 1/1990 | Reents | 600/484 |
| 4,906,926 | 3/1990 | Rogacki et al. | 324/236 |
| 5,012,206 | 4/1991 | Tigges | 331/65 |
| 5,231,359 | 7/1993 | Masuda et al. | 324/675 |
| 5,479,932 | 1/1996 | Higgins et al. | 600/529 |
| 5,515,865 | 5/1996 | Scanlon | 600/534 |

FOREIGN PATENT DOCUMENTS

| | | | |
|---|---|---|---|
| 0205931 | 12/1986 | European Pat. Off. | A61B 5/10 |
| 0557608 | 9/1993 | European Pat. Off. | G01D 5/20 |
| 2549596 | 1/1985 | France | G01B 7/00 |
| 1030314 | 5/1989 | Japan | H03H 7/01 |
| 80541 | 7/1981 | Romania | G01B 7/14 |
| 94279 | 1/1986 | Romania | G08B 13/26 |
| 9500904 | 5/1995 | Romania | G01C 23/00 |
| 9636279 | 11/1996 | WIPO | A61B 5/113 |

OTHER PUBLICATIONS

"Methods to Assess Physical Activity . . . Reference to Motion Sensors and Accelerometers", Meijer et al., IEEE Transactions On Biomedical Engineering, vol. 38, No. 3, Mar. 1991, pp. 221–229.

*Primary Examiner*—Benjamin C. Lee
*Attorney, Agent, or Firm*—Stoel Rives LLP

[57] ABSTRACT

An object sensing system (10) employs a resonant sensor (20) that receives drive energy coupled from an oscillator (12) operating at a frequency equal or close to the resonant frequency of the resonant sensor. The resonant sensor preferably includes an planar winding (60) that maximizes its distributed inductive and capacitive components, which are sensitive to a proximal conductive, nonconductive, magnetic, or nonmagnetic object (22). The resonant sensor is electrically connected in one leg of a voltage divider that produces a changing output signal voltage in response to resonant frequency changes caused by the object in proximity to the resonant sensor. The signal voltage is amplified, filtered, and processed to extract relevant data indicative of the presence, distance, movement, or proximity of the object.

30 Claims, 3 Drawing Sheets

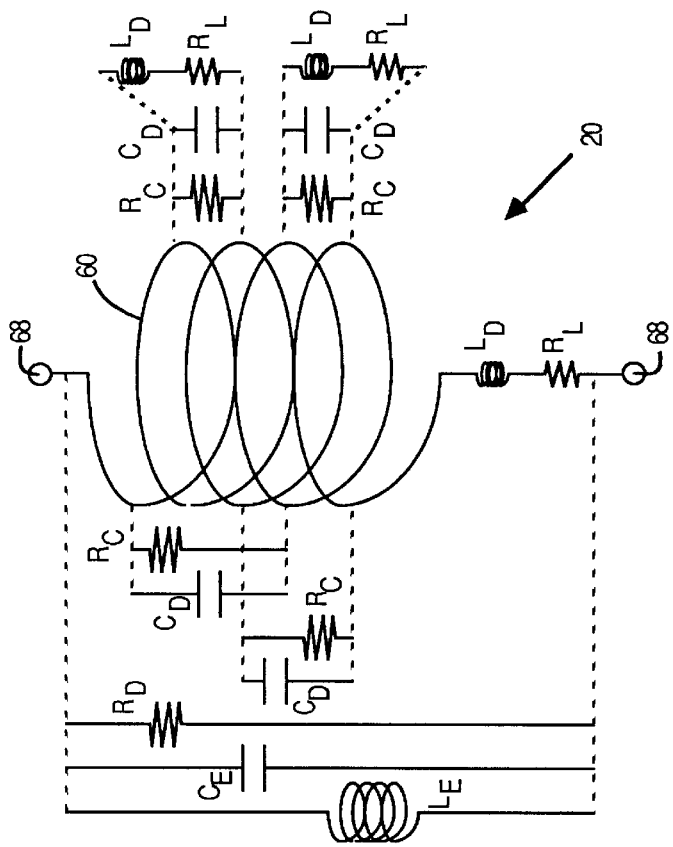
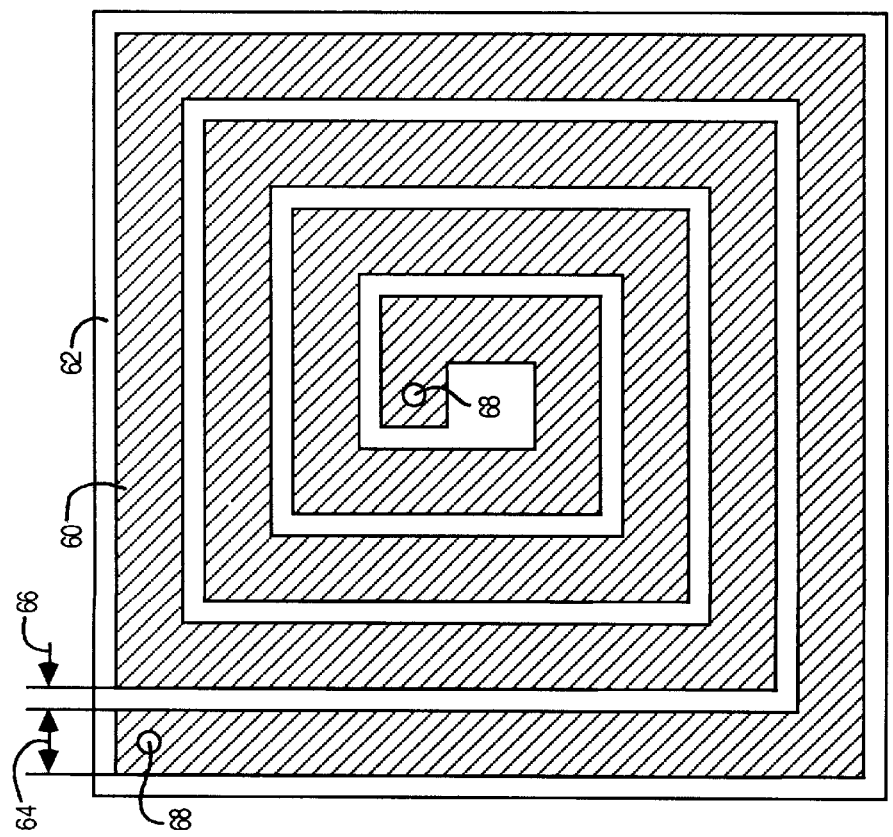
FIG. 4
FIG. 3

POSITION AND MOVEMENT REASONANT SENSOR

RELATED APPLICATIONS

This application claims priority from U.S. Provisional Pat. application No. 60/053,543, filed Jul. 23, 1997, of Horia-Nicolai Teodorescu, for POSITION AND MOVEMENT RESONANT SENSOR.

TECHNICAL FIELD

This invention relates to position and movement sensors and in particular to a resonant sensor for detecting the proximity and movement of metallic and nonmetallic objects in virtual reality, multimedia, biomedical, and industrial applications.

BACKGROUND OF THE INVENTION

There are various types of prior proximity sensors employing ultrasonic, infrared ("IR"), or electrical measurement techniques. Ultrasonic and IR sensors make proximity measurements based on reflections of ultrasonic and IR radiation. Such sensors are, however, disadvantageous in some applications because of their relatively high cost and directionality.

Electrical sensors are of various types including inductive and capacitive proximity sensors, which make measurements based on sensing a frequency change, operating regime change, or absorbed current change of an oscillator having a feedback circuit that includes the sensor. However, such electrical sensors may have at least one of the following disadvantages:

They do not provide a direct analog measurement, such as a voltage or current level, at their outputs;

they are highly susceptible to external electromagnetic fields;

they have limited sensitivity, particularly to nonmetallic objects;

they operate poorly in the vicinity of objects that have magnetic properties and/or are good electrical conductors; and they have poor high-frequency response that limits their ability to sense rapid movements and are, therefore, not useful in many biomedical, virtual reality, multimedia, and industrial applications.

What is needed, therefore, is a low-cost position and movement sensor capable of sensitively detecting metallic and nonmetallic objects and providing a direct output representing the movement, presence, or proximity of such objects.

SUMMARY OF THE INVENTION

An object of this invention is, therefore, to provide an apparatus and a method for detecting the position and movement of metallic and nonmetallic objects.

Another object of this invention is to provide a low-cost position and movement sensor that is sensitive and has good high-frequency response.

A further object of this invention is to provide a position and movement sensor that provides a direct output representing the movement, presence, or proximity of metallic and nonmetallic objects.

A position and movement sensor system of this invention employs a resonant sensor that receives drive energy coupled from an oscillator operating at a frequency equal or close to the resonant frequency of the resonant sensor. The resonant sensor includes a planar winding that maximizes its distributed inductive and capacitive components, which are sensitive to a proximal conductive, nonconductive, magnetic, or nonmagnetic object. The resonant sensor is electrically connected in one leg of a voltage divider that produces a changing output signal voltage in response to resonant frequency changes caused by the object in proximity to the resonant sensor. The signal voltage is amplified, filtered, and processed to extract relevant data indicative of the presence, distance, movement, or proximity of the object.

Additional objects and advantages of this invention will be apparent from the following detailed descriptions of preferred embodiments thereof that proceed with reference to the accompanying drawings.

BRIEF DESCRIPTION OF THE DRAWINGS

FIG. 3 is a pictorial plan view of a preferred embodiment of a resonant sensor of this invention showing its substantially planar configuration.

FIG. 4 is an electrical schematic diagram showing the parasitic distributed capacitances, inductances, and resistances of the resonant sensor of FIG. 3.

DETAILED DESCRIPTION OF PREFERRED EMBODIMENTS

Figure 1:
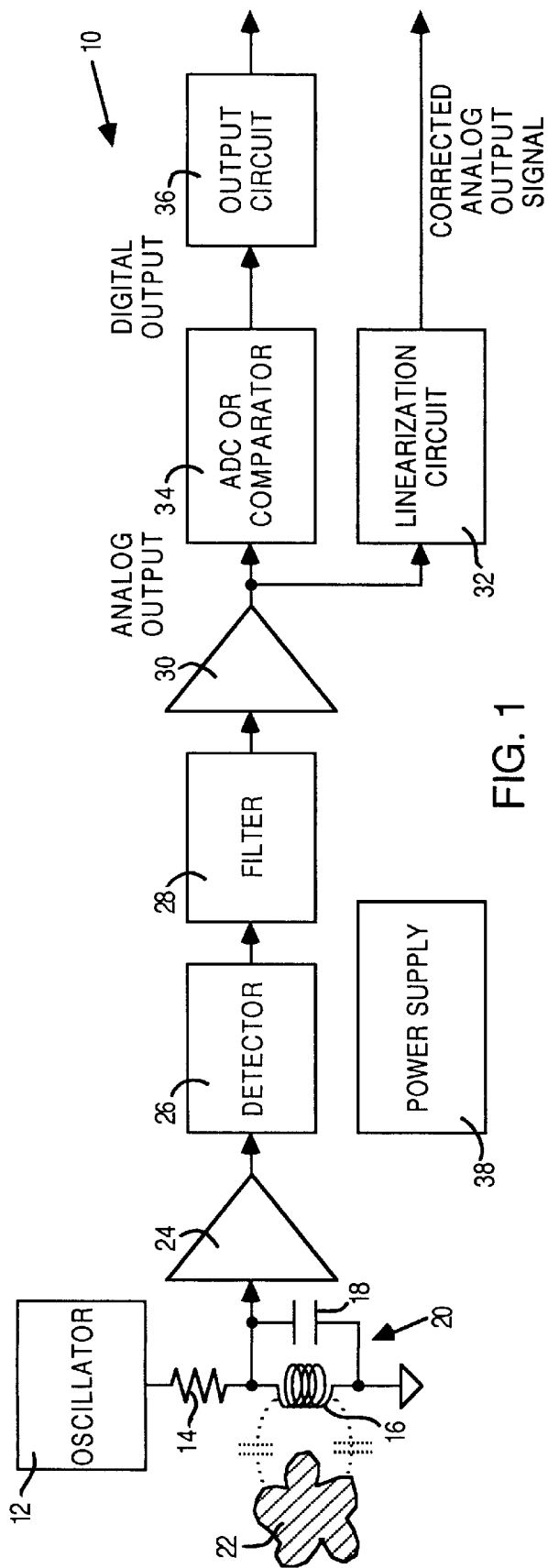
FIG. 1 is a simplified overall electrical block diagram of the position and movement sensor of this invention showing the interconnection of preferred operating elements thereof.

FIG. 1 shows a resonant sensor system 10 that includes an oscillator 12 that couples through a relatively high-impedance 14 to a sensing element 16 a signal having a predetermined frequency. Sensing element 16 is preferably an inductor that is electrically connected in parallel with its equivalent capacitance or a capacitor 18 to form a parallel resonant sensor 20 that is tuned to, or close to, the predetermined frequency of oscillator 12. High-impedance 14 and resonant sensor 20 form a voltage divider circuit that generates at their junction a signal that is directly representative of a position and/or movement of an object 22 in proximity to resonant sensor 20. In general, the proximity of object 22 to resonant sensor 20 causes a change in the parallel resonant frequency of resonant sensor 20, which causes corresponding changes in its impedance and, therefore, the magnitude of the signal across resonant sensor 20.

To minimize loading of the signal across resonant sensor 20, a high input impedance buffer amplifier 24 having a low input capacitance conveys the signal to a detector 26 that extracts a peak (or average) envelope voltage value from the signal. Skilled workers will understand how to trim the parallel resonant frequency of resonant sensor 20 to account for the input capacitance of buffer amplifier 24. The peak envelope voltage is conditioned by a filter 28 and an amplifier 30 to produce an analog output signal. In applications requiring only object movement detection or measurement, i.e., requiring only alternating current signal processing, filter 28 is preferably a band-pass filter, whereas in applications requiring object proximity detection or distance measurement, i.e., requiring direct current signal processing, filter 28 is preferably a low-pass filter.

In applications in which object 22 has a known movement frequency range, e.g., zero to f1, filter 28 is preferably a low-pass filter having a cutoff frequency of about 1.5 times f1. Filter 28 may further include multiple filtering functions to, for example, remove power supply hum (50/60 Hz and 100/120 Hz) and noise frequencies, which for example in medical applications are greater than about 150–200 Hz.

In applications requiring accurate analog measurements, a linearization circuit 32 receives the conditioned signal from amplifier 30 and applies a square-law, log, or piecewise linear conversion, as appropriate, to produce a corrected analog output signal. The correction is typically added to linearize the output voltage as a function of distance to object 22.

In applications requiring accurate digital measurements, an analog-to-digital converter ("ADC") 34 receives and digitizes the conditioned analog signal from amplifier 30 and conveys it to a digital output circuitry 36 to produce a processed digital output signal. The processing may employ square-law, log, or lookup table conversions, as appropriate, to produce a corrected digital output signal.

In applications requiring low-accuracy measurements, such as proximity sensing, ADC 34 may be replaced by a simple comparator and linearization circuit 32 and output circuitry 36 may be omitted.

Resonant sensor system 10 is powered by a conventional power supply 38.

Output circuitry 36 may further include auxiliary signal processing circuits. In a biomedical signal processing example, object 22 is a human body undergoing respiration and other movements in a bed. Resonant sensor 20 detects the movement, and the corresponding signal is conditioned through resonant sensor system 10 as generally described above. Then output circuitry 36 further processes the signal to extract desired movement frequencies, such as respiration-related frequencies, and signal predetermined alarm conditions. Preferably, band-pass filtering is used to extract the respiration-related signal, and stop-band filtering is used to extract non-respiration related signals. The filtering and extraction functions can be implemented in hardware, software, or a combination of both. Preferably, the filter frequencies are tunable to adapt to the average respiration rate of the human being monitored. In general, when sensing movements, the resonant frequency of resonant sensor 20 should be much higher (i.e., 10 times higher) than the highest object movement frequency expected.

Figure 2:
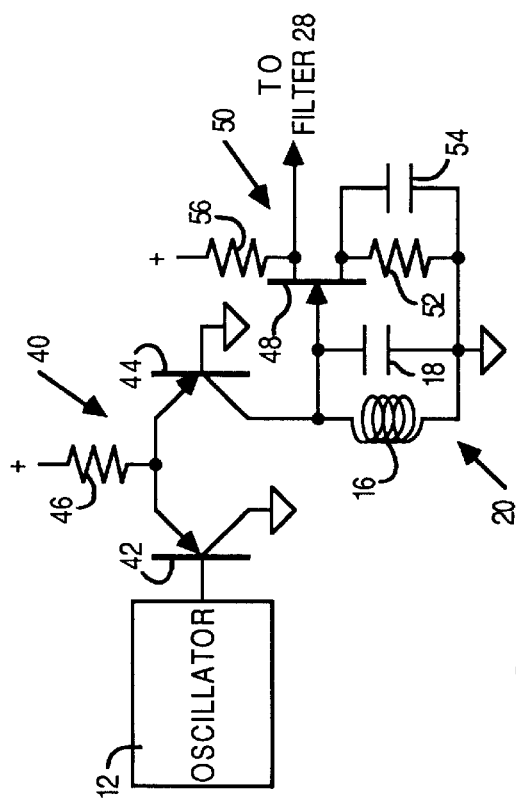
FIG. 2 is a simplified electrical schematic diagram showing alternative oscillator to sensor coupling and detector circuits of this invention.

FIG. 2 shows alternative embodiments of high impedance 14, buffer amplifier 24, and detector 26. As a general rule, the sensitivity of resonant sensor system 10 is directly proportional to the quality factor ("Q") of resonant sensor 20. A preferred embodiment of resonant sensor 20 is described below with reference to FIG. 3. Because Q is adversely affected by losses, resonant sensor 20 should be manufactured with low-loss electric and magnetic materials and loaded as lightly as practical to maintain a Q ranging from about 30 to about 100 at the operating frequency.

Major sources of loading include high-impedance 14, buffer amplifier 24, and coupling to object 22. High-impedance 14 is preferably a high-value resistor that lightly couples oscillator 12 to resonant sensor 20. The light coupling also reduces "pulling" of the predetermined frequency of oscillator 12 and reduces to an acceptable level radio frequency energy radiating from resonant sensor 20.

An alternative embodiment of high-impedance 14 is a voltage-to-current converter 40 formed by a pair of transistors 42 and 44 connected in a differential current-steering configuration in which the emitters of transistors 42 and 44 are electrically connected together and to one end of a bias current determining resistor 46. The other end of resistor 46 is connected to a fixed voltage source. Oscillator 12 is electrically connected to the base of transistor 42. The base of transistor 44 is preferably grounded. The collector of transistor 44 provides to resonant sensor 20 a high-impedance alternating current version of the voltage waveform generated by oscillator 12.

Other alternatives for reducing the loading of resonant sensor 20 by oscillator 12 include connecting high-impedance 14 to a low-impedance tap (not shown) on sensing element 16 or to a low-impedance tap (not shown) on capacitor 18, when it exists as a discrete component. Such a tapped capacitor is readily formed by electrically connecting in series a pair of capacitors having the same equivalent value as capacitor 18. The junction between the two capacitors forms the tap. A low-impedance tap is implemented by choosing one capacitance value much larger than the other and connecting one end of the larger value capacitor to ground.

An alternative embodiment of buffer amplifier 24 and detector 26 may be implemented by employing a high-input impedance field-effect transistor ("FET") 48 as a combined buffer amplifier and peak detector 50. The gate-to-source junction of FET 48 forms a diode peak detector, the detected voltage of which forms across a source resistor 52 and is stored by a capacitor 54. A buffered, and amplified if desired, version of the source voltage is developed across a drain resistor 56 connected to the drain of FET 48. Skilled workers will understand how to further combine elements of filter 28 into combined buffer amplifier and peak detector 50. Likewise, the coupling of combined buffer amplifier and peak detector 50 to resonant sensor 20 may also employ a tap as described above. Indeed, the same tap or different taps may be employed by oscillator 12 and buffer amplifier 24 or their alternative embodiments.

FIG. 3 shows a preferred embodiment of resonant sensor 20 including a planar spiral winding 60 preferably formed as a printed circuit element, but which may be bonded to, pasted on, imprinted in, deposited over, etched on, or otherwise applied to a dielectric substrate 62. Dielectric substrate 62 is preferably planar but may also be a curved surface that adapts to a shape of a supporting form (not shown) to which it is bonded, glued, or otherwise attached. Dielectric substrate 62 preferably has a low relative dielectric constant "∈" ranging from about 1.0 to about 5.0 to improve the sensitivity of resonant sensor 20 to proximal dielectric objects.

Planar winding 60 has a relatively large conductor width 64 and a relatively small spacing 66 between successive turns to achieve a suitably high capacitance between the turns and a suitably large overall capacitance for resonant sensor 20. The ratio of spacing 66 to conductor width 64 should be kept low (1:1 or less) to maximize the distributed capacitance of resonant sensor 20. The winding is shaped to provide a relatively uniform electric field in an object sensing zone that is generally determined by the overall dimensions and shape of resonant sensor 20. Such an electrical field is suitable for sensing dielectric (nonconductive and nonmagnetic) objects. Skilled workers will understand that distributing a relatively uniform electric field across a large sensing zone may conflict with developing a high distributed capacitance. Accordingly, an application dependent tradeoff may be necessary.

A suitable effective capacitance for resonant sensor 20 is achieved by forming planar winding 60 in a strip-like shape in which conductor width 64 optimizes the conductive surface area of resonant sensor 20. A large distributed capacitance is particularly useful for sensing magnetic objects that also have a high electrical conductivity, which objects are best sensed at frequencies below 1 MHz.

To further enhance sensing of magnetic objects, resonant sensor 20 may further include a magnetic core (not shown), which may be formed as a planar magnetic support or an axial element or by deposition of thin- or thick-film magnetic layers over dielectric sheets or plates.

Resonant sensor 20 may alternatively be implemented with conventional wires and bulk dielectric supports or thin- or thick-film deposition of planar winding 60. Moreover, resonant sensor 20 is not limited to a particular size or shape and may, for example, have an overall square, rectangular, elliptical, or circular shape and a size (planar area) ranging from about 1 square millimeter to about 10 square meters. For relatively small sensors, e.g., less than about 1 square centimeter, an external capacitance may be connected in parallel with terminals 68 of resonant sensor 20 to reduce its resonant frequency. However, this also decreases the sensitivity of the sensor, mainly to dielectric objects. Of course, an external capacitor may be connected in parallel with any size of resonant sensor 20 to tune it to a predetermined frequency. For the above-described shapes and sizes of resonant sensor 20, oscillator 12 operating frequency is typically in a range from about 1 MHz to about 30 MHz.

In contrast to conventional inductor/capacitor ("LC") circuits that intentionally minimize "undesirable parasitic" capacitances and couplings to surrounding objects, resonant sensor 20 of this invention enhances the parasitic capacitances and couplings and employs them as sensitive object-sensing elements.

FIG. 4 shows the equivalent electrical circuit of resonant sensor 20, which behaves as a low-loss, high Q, distributed parallel LC circuit having significant distributed capacitances, inductances, but low dissipation factors that contribute to enhanced electrical and magnetic coupling to the adjacent sensing zone. In particular, an overall equivalent capacitance $C_E$ is the effective sum of distributed capacitances $C_D$. Likewise, an overall equivalent inductance $L_E$ is the effective sum of distributed inductances $L_D$. Q is inversely proportional to an equivalent dissipation factor $R_D$, which is the effective sum of capacitance losses $R_C$ and inductance losses $R_L$. In this invention, all of these distributed elements are dependent on the proximity of surrounding objects and contribute to sensing the objects. Distributed capacitances $C_D$ and inductances $L_D$ (and possibly an external capacitance) determine the resonant frequency of resonant sensor 20. Distributed losses $R_C$ and $R_L$, which are affected by dissipation in proximal objects, determine the Q and, therefore, the sensitivity of resonant sensor 20 to dielectric objects.

For optimal sensitivity to the broadest range of object materials, it is preferred to shape resonant sensor 20 to increase distributed capacitances $C_D$ such that neither equivalent capacitor $C_E$ nor equivalent inductance $L_E$ dominates the impedance of resonant sensor 20 at the operating frequencies. Of course, it is also preferred to minimize distributed losses $R_C$ and $R_L$ such that resonant sensor has a Q ranging from about 30 to about 100. A Q greater than 100 is desirable but is technologically difficult to obtain.

Figure 5:
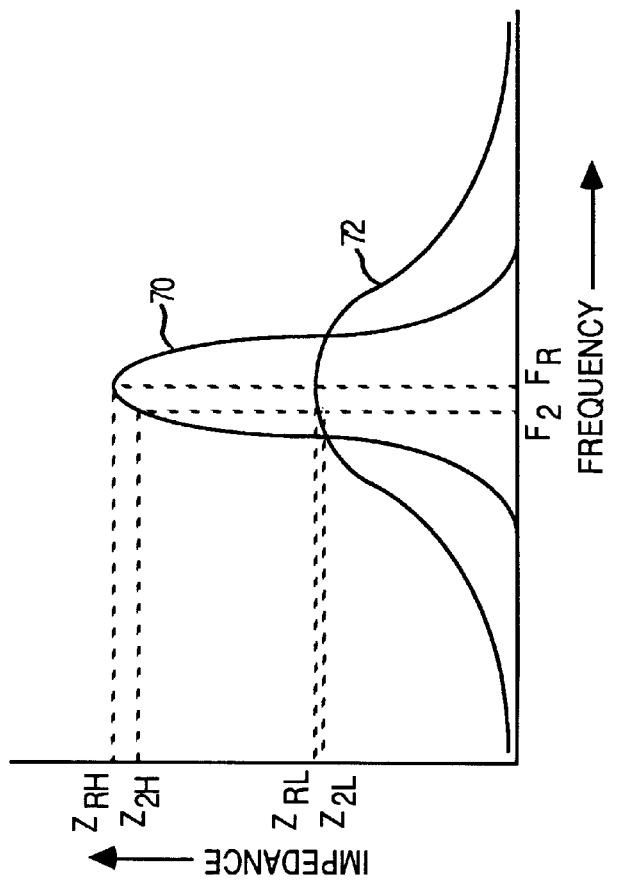
FIG. 5 is an impedance versus frequency graph showing the effect different quality factors have on the sensitivity of the resonant sensor of FIG. 3.

FIG. 5 shows the effect of Q on the sensitivity of resonant sensor 20. Referring also to FIG. 1, the voltage divider formed by high-impedance 14 and resonant sensor 20 provides an output voltage to buffer amplifier 24 that is directly proportional to the impedance of resonant sensor 20 at an operating frequency. FIG. 5 shows respective high- and low-Q impedance versus frequency curves 70 and 72 for a representative LC circuit having a resonant frequency $F_R$. At resonant frequency $F_R$, high-Q curve 70 has an impedance $Z_{RH}$ and low-Q curve 72 has an impedance $Z_{RL}$. At a second frequency $F_2$, high-Q curve 70 has an impedance $Z_{2H}$ and low-Q curve 72 has an impedance $Z_{2L}$. The impedance difference between $Z_{RH}$ and $Z_{2H}$ is clearly greater than the impedance difference between $Z_{RL}$ and $Z_{2L}$, indicating that, for a given frequency change, the impedance change for a high-Q circuit will be greater than the impedance change for a low-Q circuit. It follows that the signal voltage change versus frequency will also be greater for a high-Q circuit, resulting in higher sensitivity.

Figure 6:
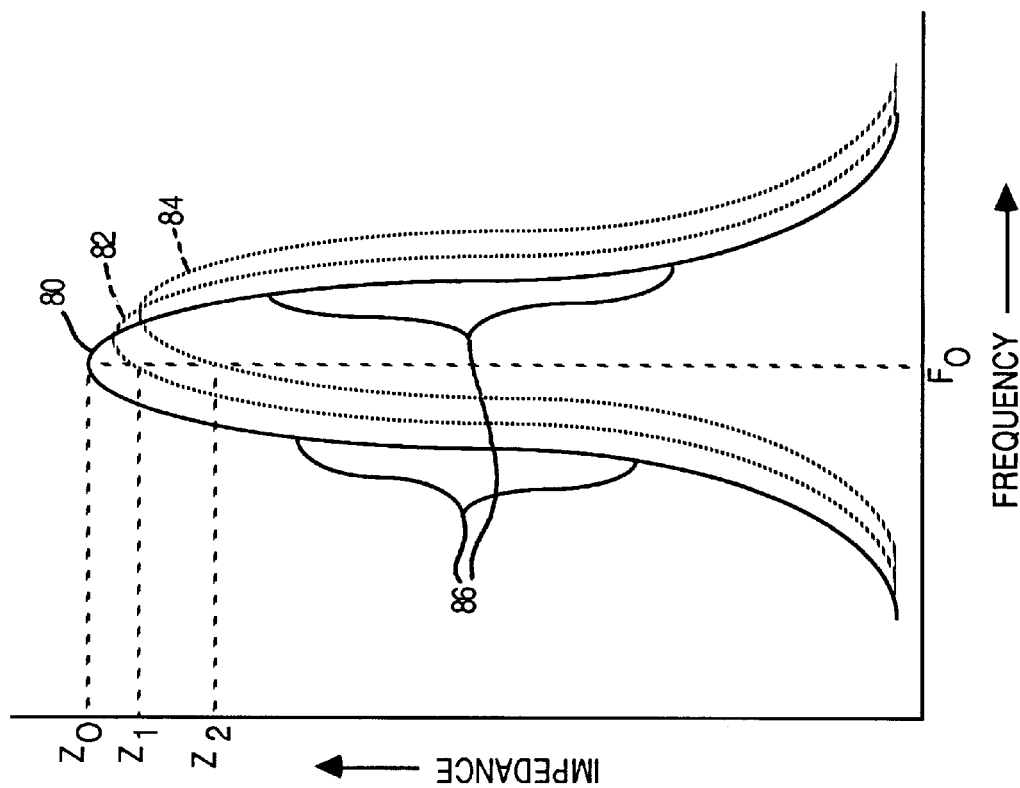
FIG. 6 is an impedance versus frequency graph for the resonant sensor of FIG. 3 showing how its impedance at a predetermined frequency changes as an external object alters the resonant frequency and quality factor of the resonant sensor.

The frequency of an LC circuit is a relative variable. That is, the resonant frequency of the LC circuit may be a constant and the operating frequency may be varied or the operating frequency may be a constant and the resonant frequency of the LC circuit may be varied. Referring to FIGS. 1 and 6, resonant sensor 20 of this invention operates according to the latter alternative in that oscillator 12 operates at a fixed operating frequency $F_O$, and the resonant frequency of resonant sensor 20 changes as a function of its proximity to object 22. Accordingly, the signal voltage across resonant sensor 20 will change in proportion to its impedance, which is determined by changes of the equivalent capacitance, inductance, or Q of resonant sensor 20.

An unloaded impedance versus frequency curve 80 shows that resonant sensor 20 has an impedance $Z_O$ at its resonant frequency, which in this case is operating frequency $F_O$. When unloaded (object 22 is not proximal), resonant sensor 20 exhibits its highest Q and impedance.

A lightly loaded impedance versus frequency curve 82 shows that the resonant frequency of resonant sensor 20 has shifted away from operating frequency $F_O$ because of the approach of object 22. At operating frequency $F_O$, resonant sensor 20 has an impedance $Z_1$. When lightly loaded, resonant sensor 20 exhibits a reduced impedance, possibly a reduced Q, and possibly a further reduced impedance as shown in FIG. 5, if object 22 increases the dissipation factor of resonant sensor 20.

A loaded impedance versus frequency curve 84 shows that the resonant frequency of resonant sensor 20 has further shifted away from operating frequency $F_o$ because of the proximity of object 22. At operating frequency $F_O$ resonant sensor 20 now has an impedance $Z_2$. When heavily loaded (object 22 is proximal), resonant sensor 20 exhibits a further reduced impedance and possibly a further reduced Q. The shifting of the curve can be in either a higher- or lower-frequency direction depending on the sensor configuration and application. The direction of frequency shifting also presents useful data when the sensor is operated in the variable frequency mode.

If resonant sensor system 10 is employed in an object proximity sensing mode, a digital output is suitable, and the resonant frequency of resonant sensor 20 should match operating frequency $F_O$.

If resonant sensor system 10 is employed in an object distance sensing mode, an analog output is suitable, and the resonant frequency of resonant sensor 20 should be either slightly lower or slightly higher than operating frequency $F_O$. Preferably, resonant sensor 20 should be tuned such that operating frequency $F_O$ is centered on a substantially linear portion 86 of impedance versus frequency curve 80 of resonant sensor 20. Two substantially linear portions 86 are shown, one above and one below the resonant frequency of resonant sensor 20, each spanning a different portion of curve 80. Skilled workers will recognize that the actual portion used will depend on the sensing application and the actual shape of curve 80.

Resonant sensor system 10 can be operated in various object sensing modes. When no magnetic, dielectric, or conductive object 22 is proximal to resonant sensor 20, its impedance is very high as indicated in curve 80. Consequently, the voltage divider signal voltage level to buffer amplifier 24 will be high.

When a magnetic object is proximal to resonant sensor 20, its equivalent inductance $L_E$ increases, lowering its resonant frequency relative to operating frequency $F_O$. Consequently, the voltage divider voltage level decreases.

Likewise, when a dielectric object 22 is proximal to resonant sensor 20, its equivalent capacitance $C_E$ increases, lowering its resonant frequency relative to operating frequency $F_O$. Consequently, the voltage divider voltage level decreases.

When a conductive object is proximal to resonant sensor 20, its equivalent capacitance $C_E$ and equivalent resistance $R_D$ increase, thereby lowering its Q and its resonant frequency relative to operating frequency $F_O$. Consequently, the voltage divider voltage level decreases.

Therefore, without regard to the nature or composition of object 22, the impedance and/or Q of resonant sensor 20 decreases at operating frequency $F_O$ as object 22 approaches, and the voltage divider voltage level decreases accordingly.

Resonant sensor system 10 of this invention is advantageous because it provides a direct analog measurement of the distance to object 22 in proximity to resonant sensor 20; it provides sensitive sensing of magnetic, nonmagnetic, conducting, and nonconductive objects; it is relatively insensitive to external electromagnetic fields because of its frequency selectivity; and it is operable in proximity to electrically conductive or magnetic objects.

Skilled workers will recognize that portions of this invention may be implemented differently from the implementations described above for preferred embodiments. For example, output circuitry 36 may alternatively include a voltage to current converter, power amplifier, or electromechanical relay to generate binary output signals suitable for initiating commands, signaling controllers, or driving alarms. Furthermore, alternatives employing a comparator may further include a variable threshold and/or a hysteresis band. The positions of resonant sensor 20 and high-impedance 14 may be interchanged, although the signal voltage level at the input of buffer amplifier 24 will be the inverse of the above-described behavior, i.e., the signal voltage level will increase when object 22 approaches resonant sensor 20.

Oscillator 12 may have a fixed operating frequency, but it is preferably tunable to a predetermined operating frequency equal or close to the resonant frequency of resonant sensor 20 when in an operating environment that includes surrounding objects having unknown properties. The analog output signal from amplifier 30 may be used as a tuning signal to match the operating frequency of oscillator 12 to the resonant frequency of resonant sensor 20. The analog output signal will peak when the frequencies are matched.

Alternatively, an automatic frequency control circuit may be implemented by employing the above-described technique and optionally activated by a switch. In this embodiment, the oscillator control voltage may be used as an output signal indicative of the presence and/or movement of object 22. Alternatively, the oscillator operating frequency can be monitored and the amount of frequency shift used to indicate the presence and/or movement of object 22.

Resonant sensor 20 may include multiple sensing elements connected in series, in parallel, or in a combination of series and parallel, to form an array of sensing elements having an overall resonant frequency or a desired range of resonant frequencies.

Finally, all the circuits may be implemented employing some combination of discrete components, integrated circuits, and hybrid circuits.

It will be obvious to those having skill in the art that many changes may be made to the details of the above-described embodiments of this invention without departing from the underlying principles thereof. Accordingly, it will be appreciated that this invention is also applicable to position and movement sensing applications other than those found in biomedical monitoring applications. The scope of the present invention should, therefore, be determined only by the following claims.

I claim:

1. An apparatus for sensing an object including at least one of a dielectric material, a conductive material, and a magnetic material, comprising:

a sensor including an inductor formed as a radially wound spiral flat conductor strip having a distributed inductance that produces a uniform magnetic field for sensing a proximity to the magnetic material, a relatively high distributed capacitance that produces a uniform electric field for sensing the proximity to the dielectric material, and a quality factor that varies as a function of the proximity to the conductive material, the sensor having an impedance that is a function of a frequency, the impedance having a maximum value when the frequency equals a resonant frequency of the sensor, the resonant frequency varying as a function of the proximity of the object to the sensor;

an oscillator generating a signal having an operating frequency that substantially equals or is close to the resonant frequency of the sensor;

a high-impedance element coupling the signal from the oscillator to the resonant sensor, the high-impedance element and the resonant sensor forming a voltage divider that produces from the signal a sensor voltage that is proportional to the impedance of the sensor and is, therefore, proportional to the proximity of the object to the sensor; and a detector extracting from the sensor voltage an output signal representative of the proximity of the object to the sensor.

2. The apparatus of claim 1 in which the quality factor has a value in a range from about 30 to about 100 when the object is not in proximity to the sensor.

3. The apparatus of claim 1 in which the radially wound spiral flat conductor strip has a width and radially spaced-apart turns separated by a distance, a ratio of the distance to the width being about 1:1 so the distributed capacitance produces a highly uniform electric field in the proximity of the object.

4. The apparatus of claim 3 in which the inductor spans a planar area ranging from about 1 square millimeter to about 10 square meters.

5. The apparatus of claim 1 in which the sensor further includes an adjustable external capacitance for adjusting the resonant frequency of the sensor.

6. The apparatus of claim 1 in which the inductor is formed over a surface of a dielectric substrate having a dielectric constant ranging from about one to about five.

7. The apparatus of claim 1 in which the sensor has a major axial surface that conforms to a predetermined curved surface configuration.

8. The apparatus of claim 1 in which the sensor includes an array of cooperating sensing elements each having an associated resonant frequency.

9. The apparatus of claim 8 in which the array of cooperating sensing elements operate together as a single global sensing element that has a parallel resonant frequency substantially equal to the operating frequency.

10. The apparatus of claim 8 in which the array of cooperating sensing elements each have a parallel resonant frequency substantially equal to the operating frequency.

11. The apparatus of claim 1 in which the high-impedance element includes at least one of a voltage to current converting transistor, a tapped inductance, and a tapped capacitance.

12. The apparatus of claim 1 in which the oscillator is tunable to the resonant frequency of the sensor.

13. The apparatus of claim 1 in which the operating frequency is in a range from about 1 MHz to about 30 MHz.

14. The apparatus of claim 1 further including a filter for extracting from the output signal at least one of an object position signal, an object movement signal, and an object presence signal.

15. The apparatus of claim 1 further including a digital signal processor for extracting from the output signal at least one of an object position signal, an object movement signal, and an object presence signal.

16. The apparatus of claim 1 in which the impedance varies with frequency along a characteristic bell-shaped curve having a substantially linear portion, and the operating frequency of the oscillator is tuned to a frequency in the substantially linear portion.

17. A method for sensing an object including at least one of a dielectric material, a conductive material, and a magnetic material, comprising:

providing a sensor including an inductor formed as a radially wound spiral flat conductor strip having a distributed inductance that produces a uniform magnetic field for sensing a proximity to the magnetic material, a relatively high distributed capacitance that produces a uniform electric field for sensing the proximity to the dielectric material, and a quality factor that varies as a function of the proximity to the conductive material, the sensor having an impedance that is a function of a frequency, the impedance having a maximum value when the frequency equals a resonant frequency of the sensor, the resonant frequency varying as a function of the proximity of the object to the sensor;

generating a signal having an operating frequency that substantially equals or is close to the resonant frequency of the sensor;

coupling the signal to the resonant sensor;

forming across the sensor a sensor voltage that is proportional to the impedance of the sensor and is, therefore, proportional to the proximity of the object to the sensor; and extracting from the sensor voltage an output signal representative of the proximity of the object to the sensor.

18. The method of claim 17 in which the radially wound spiral flat conductor strip has a width and radially spaced-apart turns separated by a distance, a ratio of the distance to the width being about 1:1.

19. The method of claim 17 in which the sensor providing step is carried out by at least one of a circuit board process, a thin film deposition process, a thick film screening process, and an integrated circuit process.

20. The method of claim 19 in which the inductor is formed over a surface of a dielectric substrate having a dielectric constant ranging from about one to about five.

21. The method of claim 17 in which the providing a sensor step includes connecting a capacitor in parallel with the inductor, and setting a capacitance of the capacitor to adjust the resonant frequency of the sensor.

22. The method of claim 17 in which the inductor has a major axial surface and the providing step further includes shaping the major axial surface to conform to a predetermined surface configuration.

23. The method of claim 17 in which the coupling step is carried out by at least one of a voltage-to-current converting transistor, a tapped inductance, and a tapped capacitance.

24. The method of claim 17 in which the extracting step includes digitally processing the output signal to produce at least one of an object position signal, an object movement signal, and an object presence signal.

25. The method of claim 17 in which the generating step includes tuning an oscillator to a resonant frequency of the sensor.

26. The method of claim 17 in which the impedance varies with frequency along a characteristic bell-shaped curve having a substantially linear portion, and the generating step includes tuning the operating frequency in the substantially linear portion.

27. A method for sensing an object, comprising:

providing a sensor having an impedance that is a function of a frequency, the impedance having a maximum value when the frequency equals a resonant frequency of the sensor, the resonant frequency varying as a function of a proximity of the object to the sensor;

generating with a voltage controlled oscillator a signal having an operating frequency that varies as a function of a voltage control signal;

coupling the signal to the resonant sensor;

forming across the sensor a sensor voltage that is proportional to the impedance of the sensor and is, therefore, related to the proximity of the object to the sensor; and deriving the voltage control signal from the sensor voltage to tune the voltage controlled oscillator to the resonant frequency of the sensor.

28. The method of claim 27 further including measuring the operating frequency of the signal and employing an amount of a frequency shift of the operating frequency as a parameter indicative of sensing the object.

29. A method for sensing an object, comprising:

providing a sensor having an impedance that is a function of a frequency, the impedance having a maximum value when the frequency equals a resonant frequency of the sensor, the resonant frequency varying as a function of a proximity of the object to the sensor;

generating a voltage-controlled oscillator signal that is tunable to an operating frequency that includes a resonant frequency of the sensor;

coupling the voltage-controlled oscillator signal to the resonant sensor;

forming across the sensor a sensor voltage that is proportional to the impedance of the sensor and is, therefore, proportional to the proximity of the object to the sensor;

extracting from the sensor voltage an output signal representative of the proximity of the object to the sensor;

deriving a voltage control signal from the output signal; and using the voltage control signal to automatically tune the voltage-controlled oscillator to the resonant frequency of the sensor.

30. The method of claim 29 in which the oscillator is tuned to the resonant frequency of the sensor by seeking a peak value of the voltage control signal.

* * * * *